(12) United States Patent
Okamoto et al.

(10) Patent No.: US 11,719,689 B2
(45) Date of Patent: Aug. 8, 2023

(54) COMPOSITION FOR SEPARATING BLOOD SERUM OR BLOOD PLASMA, BLOOD COLLECTION CONTAINER, AND METHOD FOR SEPARATING BLOOD SERUM OR BLOOD PLASMA

(71) Applicant: SEKISUI MEDICAL CO., LTD., Tokyo (JP)

(72) Inventors: Ryusuke Okamoto, Tokyo (JP); Kuniya Komai, Shunan (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 428 days.

(21) Appl. No.: 16/639,091

(22) PCT Filed: Dec. 25, 2018

(86) PCT No.: PCT/JP2018/047526
§ 371 (c)(1),
(2) Date: Feb. 13, 2020

(87) PCT Pub. No.: WO2019/131613
PCT Pub. Date: Jul. 4, 2019

(65) Prior Publication Data
US 2020/0209215 A1    Jul. 2, 2020

(30) Foreign Application Priority Data
Dec. 27, 2017 (JP) ................. 2017-251269

(51) Int. Cl.
*G01N 33/49* (2006.01)
*A61J 1/14* (2023.01)
*B01D 21/26* (2006.01)
*G01N 1/28* (2006.01)

(52) U.S. Cl.
CPC .......... *G01N 33/491* (2013.01); *A61J 1/1468* (2015.05); *B01D 21/262* (2013.01); *G01N 1/28* (2013.01); *B01D 2221/10* (2013.01)

(58) Field of Classification Search
None
See application file for complete search history.

(56) References Cited

U.S. PATENT DOCUMENTS

| | | | |
|---|---|---|---|
| 4,946,601 A | 8/1990 | Fiehler | |
| 4,994,393 A * | 2/1991 | Pradhan | G01N 33/5002 252/60 |
| 5,438,000 A | 8/1995 | Legario et al. | |
| 5,736,033 A | 4/1998 | Coleman et al. | |
| 5,888,824 A * | 3/1999 | Isogawa | G01N 33/86 436/63 |
| 2004/0129631 A1* | 7/2004 | Anraku | B01L 3/50215 585/24 |
| 2007/0187341 A1 | 8/2007 | Emerson | |
| 2008/0108493 A1 | 5/2008 | Emerson | |
| 2008/0132874 A1 | 6/2008 | Emerson | |
| 2009/0129973 A1 | 5/2009 | Emerson | |
| 2009/0139937 A1 | 6/2009 | Emerson et al. | |
| 2010/0108619 A1 | 5/2010 | Emerson | |
| 2010/0117269 A1 | 5/2010 | Emerson | |
| 2010/0267539 A1 | 10/2010 | Emerson | |
| 2010/0314335 A1 | 12/2010 | Emerson | |
| 2011/0262322 A1 | 10/2011 | Emerson | |
| 2012/0234774 A1 | 9/2012 | Emerson | |
| 2012/0258552 A1* | 10/2012 | Takahashi | G01N 33/54393 436/501 |
| 2012/0308446 A1 | 12/2012 | Inoue et al. | |
| 2013/0143727 A1 | 6/2013 | Emerson | |
| 2015/0027957 A1 | 1/2015 | Emerson | |
| 2015/0139868 A1 | 5/2015 | Emerson et al. | |
| 2018/0092806 A1 | 4/2018 | Okamoto et al. | |
| 2018/0136192 A1 | 5/2018 | Anraku et al. | |

FOREIGN PATENT DOCUMENTS

| | | |
|---|---|---|
| GB | 2 014 879 A | 9/1979 |
| JP | 56-4053 A | 1/1981 |
| JP | 58-218651 A | 12/1983 |
| JP | 61-172061 A | 8/1986 |
| JP | 6-201682 A | 7/1994 |
| JP | 2007-101322 A | 4/2007 |
| JP | 2009-286905 A | 12/2009 |
| JP | 2012-511727 A | 5/2012 |
| JP | 2013-61283 A | 4/2013 |
| WO | WO-2007/029525 A1 | 3/2007 |

(Continued)

OTHER PUBLICATIONS

The First Office Action for the Application No. 201880040289.6 from the State Intellectual Property Office of the People's Republic of China dated Aug. 30, 2021.
International Search Report for the Application No. PCT/JP2018/047526 dated Apr. 9, 2019.
Written Opinion of the International Searching Authority (PCT/ISA/237) for Application No. PCT/JP2018/047526 dated Apr. 9, 2019.
"Equipment 56 Blood collection or blood transfusion equipment General medical device, sample adjustment container for tissue culture 70369000", Apr. 2017 revision (ver. 2), Nipro Corporation, pp. 1-2.
"Nippon AEROSIL Co., Ltd. Product Guide", 10th edition, Jan. 2020, Nippon AEROSIL Co., Ltd., pp. 1-11.

(Continued)

*Primary Examiner* — Lore R Jarrett
(74) *Attorney, Agent, or Firm* — Cheng Law Group, PLLC

(57) ABSTRACT

There is provided a composition for separating blood serum or blood plasma that can inhibit bubbling during sterilization, and can inhibit the occurrence of phase separation during storage. The composition for separating blood serum or blood plasma according to the present invention comprises a (meth)acrylic acid ester-based polymer, a silica fine powder, and a silicone oil, wherein the (meth)acrylic acid ester-based polymer has fluidity at room temperature, and has a weight average molecular weight of 15000 or more and 100000 or less.

16 Claims, No Drawings

(56) References Cited

FOREIGN PATENT DOCUMENTS

WO  WO-2016/159236 A1  10/2016
WO  WO-2016/199851 A1  12/2016

OTHER PUBLICATIONS

"Safety and other information on titanium dioxide (including nanoscale titanium dioxide)", Jul. 2014, Japan Titanium Dioxide Industry Association, 15 pages.
"Silicone Foam Stabilizers for Polyurethane Foam", Dow Corning Toray Co., Ltd., pp. 1-9.
Opposition to Grant of Patent for the Japanese Patent No. 6595743 from Japan Patent Office mailed Jun. 22, 2020.
Supplementary European Search Report for the Application No. EP 18 897 844.9 dated Aug. 24, 2021.
Written Opinion of the International Searching Authority (PCT/ISA/237) for Application No. PCT/JP2018/047526 dated Apr. 9, 2019 (English Translation mailed Jul. 9, 2020).

\* cited by examiner

COMPOSITION FOR SEPARATING BLOOD SERUM OR BLOOD PLASMA, BLOOD COLLECTION CONTAINER, AND METHOD FOR SEPARATING BLOOD SERUM OR BLOOD PLASMA

TECHNICAL FIELD

The present invention relates to a composition for separating blood serum or blood plasma, and a blood collection container in which the composition for separating blood serum or blood plasma is housed in a blood collection container body. The present invention also relates to a method for separating blood serum or blood plasma that uses the blood collection container.

BACKGROUND ART

In laboratory tests, blood collection containers are widely used to collect blood samples. In a blood collection container in which a composition for separating blood serum or blood plasma is housed, the specific gravity of the separating composition is appropriately adjusted, so that blood serum or blood plasma can be separated from whole blood by means of centrifugation using differences in specific gravity.

From the viewpoint of preventing a subject from which blood is collected from bacterial infections, the interior of the blood collection container is required to be in a sterile state in conformity with the ISO and JIS standards. To sterilize the blood collection container, the container is irradiated with an electron beam, γ rays, or the like during the production process.

Patent Literature 1 listed below discloses a sealant for separating blood serum mainly comprising (A) an acrylic copolymer having a specific structure, (B) silica or bentonite, and (C) a fluorocarbon-based surfactant, a polyester-modified alkyl polysiloxane-based surfactant, or a polyether-modified alkyl polysiloxane-based surfactant.

Patent Literature 2 listed below discloses a method for sterilizing a composition for separating blood serum or blood plasma, wherein 1-alkyl-2-pyrrolidone is contained in the composition for separating blood serum or blood plasma to give a content of 0.2% by weight or more and 5% by weight or less, and the composition is irradiated with an electron beam.

CITATION LIST

Patent Literature

Patent Literature 1: Japanese Patent Laid-Open No. 6-201682
Patent Literature 2: Japanese Patent Laid-Open No. 2013-61283

SUMMARY OF INVENTION

Technical Problem

In the conventional separating composition as disclosed in Patent Literature 1, the separating composition may bubble when it is irradiated with an electron beam, γ rays, or the like for the purpose of sterilizing the interior of the blood collection container. If the separating composition bubbles, when the blood collection container is centrifuged to separate blood serum and blood clots after blood collection, the separating composition may be torn, which possibly causes the formation of oil drops or an oil film in the blood serum. If these oil drops or oil film adheres to or is built up on the specimen suction nozzle of an automatic analyzer, narrowing or clogging of the nozzle may occur, which possibly hinders accurate suction of the specimen.

In the separating composition disclosed in Patent Literature 2, bubbling of the separating composition can be inhibited to a certain extent, even if the composition is irradiated with an electron beam for the purpose of sterilizing the interior of the blood collection container. However, even the separating composition disclosed in Patent Literature 2 does not have a sufficient bubbling-inhibiting effect, and a further reduction in bubbling rate is required. Furthermore, the separating composition disclosed in Patent Literature 2 may experience a phenomenon called phase separation, in which components with low viscosity are separated and flow out during storage. The components that have flown out may also float as an oil film in blood serum or blood plasma during centrifugation after blood collection, which possibly causes the same problem as described above.

It is an object of the present invention to provide a composition for separating blood serum or blood plasma that can inhibit bubbling during sterilization, and can inhibit the occurrence of phase separation during storage. It is another object of the present invention to provide a blood collection container that houses the composition for separating blood serum or blood plasma, and a method for separating blood serum or blood plasma that uses the blood collection container.

Solution to Problem

According to a broad aspect of the present invention, there is provided a composition for separating blood serum or blood plasma comprising a (meth)acrylic acid ester-based polymer, a silica fine powder, and a silicone oil, wherein the (meth)acrylic acid ester-based polymer has fluidity at room temperature, and has a weight average molecular weight of 15000 or more and 100000 or less.

In a specific aspect of the composition for separating blood serum or blood plasma according to the present invention, the silicone oil is a polyether-modified polyalkylsiloxane.

In a specific aspect of the composition for separating blood serum or blood plasma according to the present invention, the silicone oil has an HLB value of 1 or more and 10 or less.

In a specific aspect of the composition for separating blood serum or blood plasma according to the present invention, a content of the silicone oil is 0.10% by weight or more and 2.00% by weight or less.

In a specific aspect of the composition for separating blood serum or blood plasma according to the present invention, the silica fine powder comprises hydrophilic silica.

In a specific aspect of the composition for separating blood serum or blood plasma according to the present invention, a content of the hydrophilic silica is 0.3% by weight or more and 2.20% by weight or less.

In a specific aspect of the composition for separating blood serum or blood plasma according to the present invention, the silica fine powder comprises hydrophilic silica and hydrophobic silica.

In a specific aspect of the composition for separating blood serum or blood plasma according to the present invention, a total content of the hydrophilic silica and the hydrophobic silica is 1.40% by weight or more and 4.0% by weight or less.

In a specific aspect of the composition for separating blood serum or blood plasma according to the present invention, the composition for separating blood serum or blood plasma comprises an inorganic powder different from the silica fine powder.

In a specific aspect of the composition for separating blood serum or blood plasma according to the present invention, the composition for separating blood serum or blood plasma has a specific gravity at 25° C. of 1.038 or more and 1.095 or less.

In a specific aspect of the composition for separating blood serum or blood plasma according to the present invention, the composition has a specific gravity at 25° C. of 1.038 or more and 1.050 or less.

According to a broad aspect of the present invention, there is provided a composition for separating blood plasma comprising the above-described composition for separating blood serum or blood plasma as a composition for separating blood plasma used to separate white blood cell-containing blood plasma from blood, wherein the composition has a specific gravity at 25° C. of 1.06 or more and 1.095 or less.

According to a broad aspect of the present invention, there is provided a composition for separating blood plasma comprising the above-described composition for separating blood serum or blood plasma as a composition for separating blood plasma used to separate mononuclear cell-containing blood plasma from blood, wherein the composition has a specific gravity at 25° C. of 1.060 or more and 1.085 or less.

According to a broad aspect of the present invention, there is provided a blood collection container comprising a blood collection container body; and the above-described composition for separating blood serum or blood plasma, wherein the composition for separating blood serum or blood plasma is housed in the blood collection container body.

According to a broad aspect of the present invention, there is provided a blood collection container comprising a blood collection container body; and the above-described composition for separating blood plasma, wherein the composition for separating blood plasma is housed in the blood collection container body.

According to a broad aspect of the present invention, there is provided a method for separating blood serum or blood plasma using the above-described blood collection container, comprising the steps of collecting blood into the blood collection container body; and centrifuging the blood collection container in which the blood has been collected.

According to a broad aspect of the present invention, there is provided a method for separating blood plasma using the above-described blood collection container, comprising the steps of collecting blood into the blood collection container body; and centrifuging the blood collection container in which the blood has been collected.

Advantageous Effects of Invention

A composition for separating blood serum or blood plasma according to the present invention comprises a (meth)acrylic acid ester-based polymer, a silica fine powder, and a silicone oil, wherein the (meth)acrylic acid ester-based polymer has fluidity at room temperature, and has a weight average molecular weight of 15000 or more and 100000 or less. The composition for separating blood serum or blood plasma according to the present invention, which comprises the above-described features, can inhibit bubbling during sterilization, and can inhibit the occurrence of phase separation during storage.

DESCRIPTION OF EMBODIMENTS

The present invention will be hereinafter described in detail.

A composition for separating blood serum or blood plasma according to the present invention comprises a (meth)acrylic acid ester-based polymer, a silica fine powder, and a silicone oil, wherein the (meth)acrylic acid ester-based polymer has fluidity at room temperature, and has a weight average molecular weight of 15000 or more and 100000 or less.

The composition for separating blood serum or blood plasma according to the present invention, which comprises the above-described features, can inhibit bubbling during sterilization, and can inhibit the occurrence of phase separation during storage. As a result, the composition for separating blood serum or blood plasma according to the present invention can maintain a stable blood serum- or blood plasma-separating capability over a long period of time.

For the conventional separating compositions as disclosed in Patent Literatures 1 and 2 described above, it is difficult to inhibit bubbling during sterilization and the occurrence of phase separation during storage. The present inventors have found features of a composition for separating blood serum or blood plasma whereby bubbling during sterilization and the occurrence of phase separation during storage can be inhibited. The present inventors have also found features of the composition for separating blood serum or blood plasma whereby blood plasma containing a specific blood cell component, such as white blood cells, can be separated from blood.

The composition for separating blood serum or blood plasma according to the present invention is used to separate blood serum or blood plasma from blood. The composition for separating blood serum or blood plasma according to the present invention may be used to separate blood serum from blood or separate blood plasma from blood.

Herein, the composition for separating blood serum or blood plasma used to separate blood serum from blood may be referred to as the "composition for separating blood serum", and the composition for separating blood serum or blood plasma used to separate blood plasma from blood may be referred to as the "composition for separating blood plasma".

Thus, the composition for separating blood serum or blood plasma according to the present invention is preferably the composition for separating blood serum when it is used to separate blood serum from blood, and is preferably the composition for separating blood plasma when it is used to separate blood plasma from blood. The composition for separating blood serum or blood plasma can separate blood serum and blood clots or blood plasma and a blood cell component.

By adjusting the specific gravity of the composition for separating blood serum or blood plasma according to the present invention, the composition can also be used as a composition for separating blood plasma used to separate white blood cell-containing blood plasma from blood. The white blood cell-containing blood plasma refers to blood plasma containing white blood cells (granulocytes and mononuclear cells).

The composition for separating blood plasma used to separate the white blood cell-containing blood plasma from blood may be referred herein to as the "composition for separating white blood cell-containing blood plasma". When the composition for separating white blood cell-containing blood plasma separates blood plasma from blood, it satisfies the following conditions (1A) and (2A) in the separated blood plasma:

(1A) The proportion of the number of red blood cells contained in the separated blood plasma with respect to the number of red blood cells contained in the blood before separation (the number of red blood cells contained in the separated blood plasma/the number of red blood cells contained in the blood before separation×100) is 10% or less.

(2A) The proportion of the number of white blood cells contained in the separated blood plasma with respect to the number of white blood cells contained in the blood before separation (the number of white blood cells contained in the separated blood plasma/the number of white blood cells contained in the blood before separation×100) is 25% or more.

Thus, the composition for separating blood plasma is preferably the composition for separating white blood cell-containing blood plasma. The composition for separating white blood cell-containing blood plasma can separate the white blood cell-containing blood plasma and red blood cells.

By adjusting the specific gravity of the composition for separating blood serum or blood plasma according to the present invention, the composition can also be used as a composition for separating blood plasma used to separate mononuclear cell-containing blood plasma from blood. The mononuclear cell-containing blood plasma refers to blood plasma containing mononuclear cells (lymphocytes and monocytes).

The composition for separating blood plasma used to separate the mononuclear cell-containing blood plasma from blood may be referred herein to as the "composition for separating mononuclear cell-containing blood plasma". When the composition for separating mononuclear cell-containing blood plasma separates blood plasma from blood, it satisfies all the following conditions (1B) to (3B) in the separated blood plasma:

(1B) The proportion of the number of red blood cells contained in the separated blood plasma with respect to the number of red blood cells contained in the blood before separation (the number of red blood cells contained in the separated blood plasma/the number of red blood cells contained in the blood before separation×100) is 10% or less.

(2B) The proportion of the number of granulocytes contained in the separated blood plasma with respect to the number of granulocytes contained in the blood before separation (the number of granulocytes contained in the separated blood plasma/the number of granulocytes contained in the blood before separation×100) is 50% or less.

(3B) The proportion of the number of mononuclear cells contained in the separated blood plasma with respect to the number of mononuclear cells contained in the blood before separation (the number of mononuclear cells contained in the separated blood plasma/the number of mononuclear cells contained in the blood before separation×100) is 50% or more.

Thus, the composition for separating blood plasma is preferably the composition for separating mononuclear cell-containing blood plasma. The composition for separating mononuclear cell-containing blood plasma can separate the mononuclear cell-containing blood plasma from red blood cells and granulocytes.

As described below, when blood is collected into a blood collection container in which the composition for separating blood serum or blood plasma having a particular specific gravity is housed, and the blood collection container is centrifuged, a partition wall is formed by the composition for separating blood serum or blood plasma, and blood serum or blood plasma is separated above the partition wall. The composition for separating white blood cell-containing blood plasma or the composition for separating mononuclear cell-containing blood plasma separates the white blood cell-containing blood plasma or the mononuclear cell-containing blood plasma above the partition wall.

The specific gravity at 25° C. of the composition for separating blood serum or blood plasma can be appropriately adjusted depending on the type of the blood component to be separated, for example. The specific gravity at 25° C. of the composition for separating blood serum or blood plasma is preferably 1.038 or more, more preferably 1.040 or more, preferably 1.095 or less, more preferably 1.060 or less, still more preferably 1.050 or less, and particularly preferably 1.045 or less. When the specific gravity is the above-defined lower limit or more and the above-defined upper limit or less, a partition wall having a satisfactory strength can be formed even at a low temperature or a low centrifugal force. From the viewpoint of satisfactorily separating blood serum or blood plasma containing small amounts of blood cell components from blood, the specific gravity at 25° C. of the composition for separating blood serum or blood plasma is preferably 1.038 or more, more preferably 1.040 or more, preferably 1.050 or less, and more preferably 1.045 or less.

When the composition for separating blood serum or blood plasma according to the present invention is the composition for separating blood plasma used to separate the white blood cell-containing blood plasma from blood (composition for separating white blood cell-containing blood plasma), the specific gravity at 25° C. of the composition for separating white blood cell-containing blood plasma is preferably 1.060 or more, more preferably 1.070 or more, preferably 1.095 or less, and more preferably 1.085 or less. When the specific gravity is the above-defined lower limit or more and the above-defined upper limit or less, the white blood cell-containing blood plasma can be satisfactorily separated from blood to satisfactorily obtain blood plasma containing a small amount of red blood cells, and having a high white blood cell content. For example, white blood cells can be recovered at a composition ratio equivalent to that of the white blood cell components in the blood. Furthermore, when the specific gravity is the above-defined lower limit or more and the above-defined upper limit or less, a partition wall having a satisfactory strength can be formed even at a low temperature or a low centrifugal force. Furthermore, when the specific gravity is the above-defined lower limit or more, bubbling during sterilization can be inhibited considerably.

When the composition for separating blood serum or blood plasma according to the present invention is the composition for separating blood plasma used to separate the mononuclear cell-containing blood plasma from blood (composition for separating mononuclear cell-containing blood plasma), the specific gravity at 25° C. of the composition for separating mononuclear cell-containing blood plasma is preferably 1.060 or more, more preferably 1.070 or more, preferably 1.085 or less, and more preferably 1.080 or less. When the specific gravity is the above-defined lower limit or more and the above-defined upper limit or less, the mononuclear cell-containing blood plasma can be satisfactorily separated from blood to satisfactorily obtain blood plasma containing a small amount of red blood cells, and having a high mononuclear cell content. Furthermore, when the specific gravity is the above-defined lower limit or more and the above-defined upper limit or less, a partition wall having a satisfactory strength can be formed even at a low temperature or a low centrifugal force. Furthermore, when the specific gravity is the above-defined lower limit or more, bubbling during sterilization can be inhibited considerably.

The specific gravity at 25° C. of the composition for separating blood serum or blood plasma is measured by dropping one drop of the composition for separating blood serum or blood plasma sequentially into saline solutions at 25° C. having specific gravities adjusted in a stepwise manner in increments of 0.002, and measuring the specific gravity based on floating and sinking in the saline solutions.

The following describes, for example, details of the components contained in the composition for separating blood serum or blood plasma according to the present invention.

<(Meth)Acrylic Acid Ester-Based Polymer>

The composition for separating blood serum or blood plasma according to the present invention comprises a (meth)acrylic acid ester-based polymer. As used herein, the term "(meth)acrylic acid" means one or both of acrylic acid and methacrylic acid.

The (meth)acrylic acid ester-based polymer has fluidity at room temperature. As used herein, the term "room temperature" refers to a temperature of 25° C. As used herein, the phrase "has fluidity at room temperature" means that the viscosity at 25° C. is 10 Pa·s or more and 500 Pa*s or less.

The viscosity at 25° C. of the (meth)acrylic acid ester-based polymer is preferably 30 Pa·s or more, more preferably 200 Pa*s or less, and still more preferably 150 Pa·s or less. When the viscosity is the above-defined lower limit or more and the above-defined upper limit or less, the (meth)acrylic acid ester-based polymer can have satisfactory fluidity, so that the fluidity of the composition for separating blood serum or blood plasma can be improved to improve the strength of the partition wall.

The viscosity at 25° C. is measured at 25° C. and a shear rate of $1.0\ s^{-1}$, using an E-type viscometer (for example, "TVE-35" manufactured by TOKI SANGYO CO., LTD).

From the viewpoint of inhibiting bubbling during sterilization, and from the viewpoint of allowing the partition wall to form satisfactorily, the weight average molecular weight (Mw) of the (meth)acrylic acid ester-based polymer is 15000 or more and 100000 or less. If the weight average molecular weight is less than 15000, bubbling during sterilization is likely to occur. If the weight average molecular weight is above 100000, the composition for separating blood serum or blood plasma will have a high viscosity and thus, may not form the partition wall.

The weight average molecular weight (Mw) of the (meth)acrylic acid ester-based polymer is preferably 19000 or more, more preferably 20000 or more, preferably 40000 or less, and more preferably 30000 or less. When the weight average molecular weight is the above-defined lower limit or more, bubbling during sterilization can be further inhibited. When the weight average molecular weight is the above-defined upper limit or less, the composition for separating blood serum or blood plasma can have a more satisfactory viscosity, so that the partition wall can be formed more satisfactorily.

The weight average molecular weight (Mw) represents the weight average molecular weight as measured by gel permeation chromatography (GPC) relative to polystyrene.

The (meth)acrylic acid ester-based polymer is obtained by polymerizing at least one (meth)acrylic acid ester monomer. The (meth)acrylic acid ester-based polymer has a structural unit derived from the at least one (meth)acrylic acid ester monomer. The (meth)acrylic acid ester-based polymer may have a structural unit derived from a monomer other than the (meth)acrylic acid ester monomer. That is, the (meth)acrylic acid ester-based polymer may be a homopolymer of one (meth)acrylic acid ester monomer, a copolymer of two or more (meth)acrylic acid ester monomers, or a copolymer of at least one (meth)acrylic acid ester monomer with a monomer other than the (meth)acrylic acid ester monomer. As the (meth)acrylic acid ester-based polymer, only one (meth)acrylic acid ester-based polymer may be used, or two or more (meth)acrylic acid ester-based polymers may be used in combination.

Examples of the (meth)acrylic acid ester monomer include (meth)acrylic acid alkyl esters having an alkyl group containing 1 to 20 carbon atoms, (meth)acrylic acid polyalkylene glycol esters, (meth)acrylic acid alkoxyalkyl esters, (meth)acrylic acid hydroxyalkyl esters, (meth)acrylic acid glycidyl esters, (meth)acrylic acid dialkylaminoalkyl esters, (meth)acrylic acid benzyl esters, (meth)acrylic acid phenoxyalkyl esters, (meth)acrylic acid cyclohexyl esters, (meth)acrylic acid isobornyl esters, and (meth)acrylic acid alkoxysilylalkyl esters. As the (meth)acrylic acid ester monomer, only one (meth)acrylic acid ester monomer may be used, or two or more (meth)acrylic acid ester monomers may be used in combination.

Preferably, two or more (meth)acrylic acid ester monomers are used as the (meth)acrylic acid ester monomer. When two or more (meth)acrylic acid ester monomers are used, the content ratio between the (meth)acrylic acid ester monomers having different molecular structures can be adjusted, so that the specific gravity and the viscosity of the resulting (meth)acrylic acid ester-based polymer can be readily adjusted.

The content of the (meth)acrylic acid ester monomer is preferably 50% by weight or more, more preferably 60% by weight or more, and still more preferably 70% by weight or more, based on 100% by weight of the (meth)acrylic acid ester-based polymer. The upper limit of the content of the (meth)acrylic acid ester monomer based on 100% by weight of the (meth)acrylic acid ester-based polymer is not specifically limited. The content of the (meth)acrylic acid ester monomer may be 100% by weight (total weight), less than 100% by weight, 90% by weight or less, or 80% by weight or less, based on 100% by weight of the (meth)acrylic acid ester-based polymer. When the content of the (meth)acrylic acid ester monomer is the above-defined lower limit or more, the composition for separating blood serum or blood plasma can have a more satisfactory viscosity, so that the strength of the partition wall can be further increased.

Examples of the monomer other than the (meth)acrylic acid ester monomer include a radically polymerizable monomer capable of radical copolymerization with the (meth)acrylic acid ester monomer.

Examples of the radically polymerizable monomer include aromatic vinyl monomers, vinyl esters, vinyl ethers, vinyl pyrrolidone, and (meth)allyl ethers. As the radically polymerizable monomer, only one radically polymerizable monomer may be used, or two or more radically polymerizable monomers may be used in combination.

Examples of the aromatic vinyl monomers include styrene, α-methylstyrene, p-methylstyrene, α-methyl-p-methylstyrene, p-methoxystyrene, o-methoxystyrene, 2,4-dimethylstyrene, chlorostyrene, and bromostyrene.

Examples of the vinyl esters include (meth)acrylate, maleate anhydride, fumarate, (meth)acrylamide, dialkyl (meth)acrylamide, and vinyl acetate.

The radically polymerizable monomer is preferably the aromatic vinyl monomer. Because the aromatic vinyl monomer has a high specific gravity and high hydrophobicity, it can further inhibit the adsorption of a drug in the blood to the composition for separating blood serum or blood plasma, while maintaining the blood serum- or blood plasma-separating capability of the composition for separating blood serum or blood plasma. Furthermore, a copolymer obtained by copolymerization of the aromatic vinyl monomer with the (meth)acrylic acid ester monomer is less likely to have an increase in molecular weight due to repolymerization of the molecular chain, during sterilization using an electron beam or γ rays, as compared with a (meth)acrylic acid ester-based polymer not having a structure derived from the aromatic vinyl monomer. Thus, the viscosity of the (meth)acrylic acid ester-based polymer can be maintained satisfactorily.

From the viewpoint of even further inhibiting the adsorption of a drug in the blood to the composition for separating blood serum or blood plasma, and from the viewpoint of maintaining the viscosity of the (meth)acrylic acid ester-based polymer more satisfactorily, the aromatic vinyl monomer is preferably styrene or α-methylstyrene.

The (meth)acrylic acid ester-based polymer can be obtained using a standard radical polymerization method. Examples of the radical polymerization method include the solution polymerization method, the bulk polymerization method, the dispersion polymerization method, and the living radical polymerization method.

The specific gravity at 25° C. of the (meth)acrylic acid ester-based polymer is preferably 1.030 or more, preferably 1.070 or less, more preferably 1.050 or less, and still more preferably 1.035 or less. When the specific gravity is the above-defined upper limit or less, the specific gravity of the composition for separating blood serum or blood plasma does not become excessively high, and the partition wall can be formed satisfactorily. When the specific gravity is the above-defined lower limit or more, the specific gravity of the composition for separating blood serum or blood plasma can be adjusted satisfactorily without adding a large amount of the silica fine powder. If a large amount of the silica fine powder is added, the fluidity of the composition for separating blood serum or blood plasma may decrease due to, for example, the agglomeration of the silica fine powder that occurs with time, and the partition wall may not be formed satisfactorily.

The specific gravity at 25° C. is measured by dropping one drop of the (meth)acrylic acid ester-based polymer sequentially into saline solutions at 25° C. having specific gravities adjusted in a stepwise manner in increments of 0.002, and measuring the specific gravity based on floating and sinking in the saline solutions.

<Silica Fine Powder>

The composition for separating blood serum or blood plasma according to the present invention comprises a silica fine powder. The silica fine powder is a powder component mainly containing silicon dioxide. As the silica fine powder, only one silica fine powder may be used, or two or more silica fine powders may be used in combination.

Examples of the silica fine powder include natural silica and synthetic silica. Examples of synthetic silica include hydrophilic silica and hydrophobic silica. The silica fine powder is preferably synthetic silica, which is stable in quality, and is more preferably synthetic silica prepared using the vapor-phase method.

Hydrophilic silica, in which hydroxy groups on the surface of the particles are hydrogen-bonded to each other, serves to impart thixotropy to the composition for separating blood serum or blood plasma, and adjust the specific gravity. On the other hand, hydrophobic silica only serves to adjust the specific gravity, because hydroxy groups on the surface of the particles are substituted with hydrophobic groups, such as methylsilane, and thus do not form hydrogen bonding.

From the viewpoint of maintaining both the specific gravity and the thixotropy of the composition for separating blood serum or blood plasma in a suitable range, the silica fine powder preferably comprises hydrophilic silica.

The content of the hydrophilic silica is preferably 0.3% by weight or more, more preferably 0.5% by weight or more, still more preferably 0.7% by weight or more, preferably 2.20% by weight or less, and more preferably 2.00% by weight or less, based on 100% by weight of the composition for separating blood serum or blood plasma. When the content of the hydrophilic silica is the above-defined lower limit or more and the above-defined upper limit or less, both the specific gravity and the thixotropy of the composition for separating blood serum or blood plasma can be maintained in a more suitable range.

When the hydrophilic silica only is not sufficient to maintain both the specific gravity and the thixotropy of the composition for separating blood serum or blood plasma in a suitable range, the composition for separating blood serum or blood plasma preferably contains hydrophobic silica in addition to the hydrophilic silica, in order to adjust the thixotropy and the specific gravity of the composition for separating blood serum or blood plasma in a suitable range. That is, the composition for separating blood serum or blood plasma preferably comprises hydrophilic silica and hydrophobic silica.

The total content of the hydrophilic silica and the hydrophobic silica (the sum of the content of the hydrophilic silica and the content of the hydrophobic silica) is preferably 1.40% by weight or more, more preferably 1.50% by weight or more, preferably 4.0% by weight or less, more preferably 3.5% by weight or less, and still more preferably 2.50% by weight or less, based on 100% by weight of the composition for separating blood serum or blood plasma. When the total content is the above-defined lower limit or more and the above-defined upper limit or less, a satisfactory specific gravity and satisfactory thixotropy of the composition for separating blood serum or blood plasma can be achieved. The method for adjusting the total content in the above-defined preferable range is, for example, as follows: The content of the hydrophilic silica is determined so that the thixotropy of the composition for separating blood serum or blood plasma falls within a suitable range. With this content of the hydrophilic silica, if the specific gravity of the composition for separating blood serum or blood plasma falls below the suitable range, hydrophobic silica is further incorporated into the composition for separating blood serum or blood plasma in an amount corresponding to the insufficiency of the content. While various methods are known for evaluating thixotropy, the below-described evaluation of flow is suitable for evaluating the thixotropy of the composition for separating blood serum or blood plasma.

The average particle diameter of the silica fine powder is not specifically limited. The average particle diameter of the silica fine powder may be 1 nm or more, or 10 nm or more, or may be 500 nm or less, or 100 nm or less.

The average particle diameter of the silica fine powder is the average diameter as measured in volume, and is the value of the median diameter (D50) at 50%. The volume average particle diameter (D50) can be measured using the laser diffraction/scattering method, the image analysis method, the Coulter method, the centrifugal sedimentation method, or the like. The volume average particle diameter (D50) of the silica fine powder is preferably determined by performing measurement using the laser diffraction/scattering method or the image analysis method.

Examples of commercial products of the hydrophilic silica include the AEROSIL series, such as AEROSIL (registered trademark) 90G, 130, 200, 300, 200CF, and 300CF (manufactured by NIPPON AEROSIL CO., LTD.), the REOLOSIL series, such as REOLOSIL (registered trademark) QS-10, QS-20, and QS-30 (manufactured by Tokuyama Corporation), and the WACKER HDK series, such as WACKER HDK S13, N20, and T30 (manufactured by Wacker Asahikasei Silicone Co., Ltd.). The above-described commercial products of hydrophilic silica are hydrophilic silica prepared using the vapor-phase method, and are easy to use.

Examples of commercial products of the hydrophobic silica include the AEROSIL series, such as AEROSIL R972, R974, R805, and R812 (manufactured by NIPPON AEROSIL CO., LTD.), the REOLOSIL series, such as REOLOSIL MT-10, DM-30S, HM-30S, KS-20S, and PM-20 (manufactured by Tokuyama Corporation), and the WACKER HDK series, such as WACKER HDK H15, H18, and H30 (manufactured by Wacker Asahikasei Silicone Co., Ltd.). The above-described commercial products of hydrophobic silica are hydrophobic silica prepared using the vapor-phase method, and are easy to use.

<Silicone Oil>

The composition for separating blood serum or blood plasma according to the present invention comprises a silicone oil. Because the composition for separating blood serum or blood plasma comprises a silicone oil, satisfactory thixotropy and satisfactory dispersibility of the silica fine powder can be achieved, and the occurrence of phase separation can be inhibited. As the silicone oil, only one silicone oil may be used, or two or more silicone oils may be used in combination.

Examples of the silicone oil include dimethyl silicone oils, methyl phenyl silicone oils, methyl hydrogen silicone oils, alkyl-modified silicone oils, aralkyl-modified silicone oils, fluorine-modified silicone oils, polyether-modified silicone oils, amino-modified silicone oils, epoxy-modified silicone oils, phenol-modified silicone oils, carboxy-modified silicone oils, methacrylate-modified silicone oils, and alkoxy-modified silicone oils.

Examples of commercial products of the dimethyl silicone oils include BY16-873 and PRX413 (manufactured by Dow Corning Toray Co., Ltd.).

Examples of commercial products of the methyl phenyl silicone oils include SH510-100CS, SH510-500CS, SH550, and SH710 (manufactured by Dow Corning Toray Co., Ltd.).

Examples of commercial products of the methyl hydrogen silicone oils include SH1107 (manufactured by Dow Corning Toray Co., Ltd.).

Examples of commercial products of the alkyl-modified silicone oils include SH203, SH230, SF8416, and BY16-846 (manufactured by Dow Corning Toray Co., Ltd.).

Examples of commercial products of the fluorine-modified silicone oils include FS1265-300CS, FS1265-1,000CS, and FS1265-10,000CS (manufactured by Dow Corning Toray Co., Ltd.).

Examples of the polyether-modified silicone oils include polyether-modified polyalkylsiloxanes. Examples of commercial products of the polyether-modified silicone oils include BY16-201, SF8410, SF8427, SF8428, FZ-2162, SH3746, SH3749, FZ-77, L-7001, Y7006, FZ-2104, FZ-2110, SH8400, SH8410, SH3773M, FZ-2207, FZ-2203, FZ-2222, and FZ-2208 (manufactured by Dow Corning Toray Co., Ltd.).

Examples of commercial products of the amino-modified silicone oils include BY16-871, BY16-853U, FZ-3705, SF8417, BY16-849, FZ-3785, BY16-890, BY16-208, BY16-893, FZ-3789, BY16-878, and BY16-891 (manufactured by Dow Corning Toray Co., Ltd.).

Examples of commercial products of the epoxy-modified silicone oils include BY16-855, SF8411, SF8413, BY16-839, and SF8421 (manufactured by Dow Corning Toray Co., Ltd.).

Examples of commercial products of the carboxy-modified silicone oils include BY16-880 (manufactured by Dow Corning Toray Co., Ltd.).

The silicone oil is preferably an alkyl-modified silicone oil, an aralkyl-modified silicone oil, a fluoro-modified silicone oil, or a polyether-modified silicone oil, and more preferably a polyether-modified polyalkylsiloxane. In this case, more satisfactory thixotropy and more satisfactory dispersibility of the silica fine powder can be achieved, and the occurrence of phase separation can be further inhibited.

The silicone oil has an HLB (Hydrophilic Lipophilic Balance) value of preferably 1 or more, more preferably 2 or more, still more preferably 4 or more, particularly preferably 5.5 or more, most preferably 6 or more, preferably 10 or less, more preferably 8 or less, still more preferably 7.5 or less, and particularly preferably 7 or less. When the HLB value is the above-defined lower limit or more, satisfactory thixotropy can be achieved, and the composition for separating blood serum or blood plasma is unlikely to flow during the storage of the blood collection container. When the HLB value is the above-defined upper limit or less, the occurrence of phase separation can be even further inhibited.

The HLB value represents the HLB value based on the Davies' method. The HLB value assumes a value of 0 or more and 20 or less; the lower the HLB value is, the stronger the hydrophobicity (lipophilicity) is, and the higher the HLB value is, the stronger the hydrophilicity is. The HLB value based on the Davies' method is calculated in accordance with the following equation:

<HLB value=7+(sum of hydrophilic group numbers)−(sum of lipophilic group numbers)> wherein the group number refers to a specific numerical value assigned to each functional group.

The content of the silicone oil is preferably 0.10% by weight or more, more preferably 0.15% by weight or more, preferably 2.00 by weight or less, and more preferably 0.5% by weight or less, based on 100% by weight of the composition for separating blood serum or blood plasma. When the content of the silicone oil is the above-defined lower limit or more and the above-defined upper limit or less, the occurrence of phase separation can be still further inhibited.

<Inorganic Powder>

The composition for separating blood serum or blood plasma according to the present invention may comprise an inorganic powder different from the silica fine powder. When the composition for separating blood serum or blood plasma according to the present invention is the composition for separating blood plasma used to separate the white blood cell-containing blood plasma or the mononuclear cell-containing blood plasma from blood (composition for separating white blood cell-containing blood plasma or composition for separating mononuclear cell-containing blood plasma), the composition for separating blood plasma preferably comprises the inorganic powder. The inorganic powder is used as a specific gravity-adjusting component. As the inorganic powder, only one inorganic powder may be used, or two or more inorganic powders may be used in combination.

Examples of the inorganic powder include titanium oxide powder, zinc oxide powder, alumina powder, glass fine powder, talc powder, kaolin powder, bentonite powder, titania powder, and zirconium powder.

From the viewpoint of maintaining the thixotropy and the specific gravity in a suitable range, the inorganic powder is preferably titanium oxide powder or zinc oxide powder.

The specific gravity of the inorganic powder is preferably greater than that of the silica fine powder. The specific gravity of the inorganic powder is preferably greater than that of the silica fine powder by 1 or more, and more preferably 2 or more. In this case, the specific gravity of the composition for separating blood plasma can be effectively increased, and thus, the composition for separating blood plasma can be suitably used as the composition for separating white blood cell-containing blood plasma and the composition for separating mononuclear cell-containing blood plasma.

The specific gravity of the inorganic powder is preferably 3 or more, and more preferably 4 or more. The inorganic powder preferably has a greater specific gravity. When the specific gravity is the above-defined lower limit or more, the specific gravity of the composition for separating blood plasma can be effectively increased, and thus, the composition for separating blood plasma can be suitably used as the composition for separating white blood cell-containing blood plasma and the composition for separating mononuclear cell-containing blood plasma.

The average particle diameter of the inorganic powder is not specifically limited. The average particle diameter of the inorganic powder may be 10 nm or more, or 100 nm or more, or may be 10 µm or less, or 1 µm or less.

The average particle diameter of the inorganic powder is the average diameter as measured in volume, and is the value of the median diameter (D50) at 50%. The volume average particle diameter (D50) can be measured using the laser diffraction/scattering method, the image analysis method, the Coulter method, the centrifugal sedimentation method, or the like. The volume average particle diameter (D50) of the inorganic powder is preferably determined by performing measurement using the laser diffraction/scattering method or the image analysis method.

When the composition for separating blood serum or blood plasma according to the present invention is the composition for separating white blood cell-containing blood plasma or the composition for separating mononuclear cell-containing blood plasma, it preferably satisfies the following: The content of the inorganic powder is preferably 0.01% by weight or more, more preferably 0.1% by weight or more, still more preferably 1% by weight or more, preferably 10% by weight or less, and more preferably 5% by weight or less, based on 100% by weight of the composition for separating white blood cell-containing blood plasma or 100% by weight of the composition for separating mononuclear cell-containing blood plasma. When the content of the inorganic powder is the above-defined lower limit or more and the above-defined upper limit or less, the effects of the present invention can be achieved more effectively. Furthermore, when the content of the inorganic powder is the above-defined lower limit or more and the above-defined upper limit or less, the composition for separating blood serum or blood plasma according to the present invention can be suitably used as the composition for separating white blood cell-containing blood plasma or the composition for separating mononuclear cell-containing blood plasma.

<Other Components>

The composition for separating blood serum or blood plasma according to the present invention may contain other components other than the above-described components, as long as the effects of the present invention are not impaired. The composition for separating blood serum or blood plasma according to the present invention may contain an antioxidant and a colorant, for example, as the other components. As each of the other components, only one component may be used, or two or more components may be used in combination.

<Method for Producing Composition for Separating Blood Serum or Blood Plasma>

The method for producing the composition for separating blood serum or blood plasma according to the present invention is not specifically limited. The composition for separating blood serum or blood plasma can be produced by, for example, mixing the (meth)acrylic acid ester-based polymer, the silica fine powder, and the silicone oil with the inorganic powder and the other components that may be optionally blended. The mixing method is not specifically limited, and mixing may be performed using a known mixer, such as a planetary mixer, a ball mill, or a disperser.

From the viewpoint of achieving more satisfactory thixotropy and more satisfactory dispersibility of the silica fine powder, the composition for separating blood serum or blood plasma is preferably produced by mixing the (meth)acrylic acid ester-based polymer, the silica fine powder, and the inorganic powder that may be optionally blended, and then adding, to the resulting mixture, the silicone oil and the other components that may be optionally blended, and further mixing them.

<Blood Collection Container>

A blood collection container according to the present invention comprises a blood collection container body; and the composition for separating blood serum or blood plasma, wherein the composition for separating blood serum or blood plasma is housed in the blood collection container body.

When the composition for separating blood serum or blood plasma is the composition for separating blood plasma used to separate the white blood cell-containing blood plasma or the mononuclear cell-containing blood plasma (composition for separating white blood cell-containing blood plasma or composition for separating mononuclear cell-containing blood plasma), the blood collection container according to the present invention comprises a blood collection container body and the composition for separating blood plasma. The composition for separating blood plasma is housed in the blood collection container body.

While the material of the blood collection container body is not specifically limited, examples include known materials, for example, thermoplastic resins, such as polyethylene (PE), polypropylene (PP), polystyrene (PS), polyethylene terephthalate (PET), polymethyl methacrylate, polyacrylonitrile, polyamide, acrylonitrile-styrene copolymers, and ethylene-vinyl alcohol copolymers; thermosetting resins, such as unsaturated polyester resins, epoxy resins, and epoxy-acrylate resins; modified natural resins, such as cellulose acetate, cellulose propionate, ethyl cellulose, and ethylchitin; silicates, such as soda-lime glass, phosphosilicate glass, and borosilicate glass, glasses, such as quartz glass, and combinations of the above, or materials mainly containing any of the above.

The blood collection container body may be sealed with a sealing member, such as a stopper or an aluminum seal.

The internal pressure of the blood collection container is not specifically limited. The blood collection container can also be used as a vacuum blood collection tube in which the interior is evacuated, and which is sealed with the sealing member. When the blood collection container is the vacuum blood collection tube, a predetermined amount of blood can be easily collected irrespective of the skill of the person who collects blood.

From the viewpoint of preventing bacterial infections, the interior of the blood collection container is preferably sterilized in compliance with the criteria defined in ISO and JIS.

Depending on the purpose such as blood clot adhesion prevention or blood coagulation acceleration, a known drug, such as a blood clot adhesion-preventing component or a blood coagulation accelerator, may be adhered to the interior wall of the blood collection container body.

When the blood collection container is used to separate blood plasma from blood, an anticoagulant is preferably housed in the blood collection container body. In this case, the anticoagulant may be adhered to the interior wall of the blood collection container body. Alternatively, the anticoagulant may be added to the collected blood. Examples of the anticoagulant include heparin, ethylenediaminetetraacetic acid (EDTA), and citric acid.

When the blood collection container is used to separate blood serum from blood, the anticoagulant is preferably not housed in the blood collection container body.

<Method for Separating Blood Serum or Blood Plasma>

A method for separating blood serum or blood plasma according to the present invention is a method for separating blood serum or blood plasma that uses the above-described blood collection container. The method for separating blood serum or blood plasma according to the present invention preferably comprises the steps of collecting blood into the above-described blood collection container body (blood-collecting step); and centrifuging the blood collection container in which the blood has been collected (centrifuging step).

The method for separating blood serum or blood plasma may be a method for separating blood serum from blood (method for separating blood serum), or may be a method for separating blood plasma from blood (method for separating blood plasma). The method for separating blood plasma from blood may be a method for separating the white blood cell-containing blood plasma from blood (method for separating white blood cell-containing blood plasma), or may be a method for separating the mononuclear cell-containing blood plasma from blood (method for separating mononuclear cell-containing blood plasma).

Thus, when the composition for separating blood serum or blood plasma is the composition for separating blood plasma used to separate the white blood cell-containing blood plasma or the mononuclear cell-containing blood plasma from blood (composition for separating white blood cell-containing blood plasma or composition for separating mononuclear cell-containing blood plasma), the method for separating blood plasma preferably comprises the following features: the step of collecting blood into a blood collection container body in which the composition for separating blood plasma, which is the composition for separating white blood cell-containing blood plasma or the composition for separating mononuclear cell-containing blood plasma, is housed (blood-collecting step); and centrifuging the blood collection container in which the blood has been collected (centrifuging step).

The method for separating blood serum or blood plasma according to the present invention can separate and recover blood serum or specific blood plasma from blood easily at a high recovery rate. In particular, the method for separating blood serum or blood plasma according to the present invention can effectively reduce the amount of red blood cells contained in the separated blood serum, blood plasma, white blood cell-containing blood plasma, and mononuclear cell-containing blood plasma. Furthermore, the method for separating white blood cell-containing blood plasma and the method for separating mononuclear cell-containing blood plasma can inhibit damage to white blood cells, mononuclear cells, and the like.

Method for Separating Blood Serum:

The method for separating blood serum uses the above-described composition for separating blood serum as the composition for separating blood serum or blood plasma housed in the blood collection container body.

The centrifugation conditions in the method for separating blood serum are not specifically limited, as long as the partition wall can be formed by the composition for separating blood serum to separate blood clots and blood serum. Examples of the centrifugation conditions include centrifuging at 400 G or more and 4000 G or less for 10 minutes or more and 120 minutes or less. In the centrifuging step, the blood clots are positioned below and the blood serum is positioned above the partition wall formed by the composition for separating blood serum.

Method for Separating Blood Plasma:

The method for separating blood plasma uses the above-described composition for separating blood plasma as the composition for separating blood serum or blood plasma housed in the blood collection container body. Preferably, in the blood-collecting step, the anticoagulant is housed in the blood collection container body, or blood to which the anticoagulant has been added is collected into the blood collection container body. When the composition for separating white blood cell-containing blood plasma is used as the composition for separating blood plasma, the white blood cell-containing blood plasma can be separated, and when the composition for separating mononuclear cell-containing blood plasma is used as the composition for separating blood plasma, the mononuclear cell-containing blood plasma can be separated.

The centrifugation conditions in the method for separating blood plasma are not specifically limited, as long as the partition wall can be formed by the composition for separating blood plasma to separate a blood cell component and blood plasma. Examples of the centrifugation conditions include centrifuging at 400 G or more and 4000 G or less for 10 minutes or more and 120 minutes or less. In the centrifuging step, the blood cell component is positioned below and the blood plasma is positioned above the partition wall formed by the composition for separating blood plasma. When the composition for separating white blood cell-containing blood plasma is used as the composition for separating blood plasma, the blood cell component including red blood cells is positioned below and the white blood cell-containing blood plasma is positioned above the partition wall formed by the composition for separating white blood cell-containing blood plasma, in the centrifuging step. When the composition for separating mononuclear cell-containing blood plasma is used as the composition for separating blood plasma, the blood cell component including red blood cells and granulocytes is positioned below and the mononuclear cell-containing blood plasma is positioned above the partition wall formed by the composition for separating mononuclear cell-containing blood plasma, in the centrifuging step.

The specific gravities of blood plasma, red blood cells, white blood cells, granulocytes, and mononuclear cells are typically as follows:
  specific gravity of blood plasma: 1.025 to 1.030
  specific gravity of red blood cells: 1.090 to 1.120
  specific gravity of white blood cells: 1.055 to 1.110
  specific gravity of granulocytes: 1.070 to 1.110
  specific gravity of mononuclear cells: 1.055 to 1.080

The present invention will be hereinafter described in more detail using Examples. The present invention is not limited solely to the following Examples.

The following materials were prepared as the materials of compositions for separating blood serum or blood plasma.

<Silica Fine Powder>
Hydrophilic silica (trade name "200CF" manufactured by NIPPON AEROSIL CO., LTD., specific gravity: 2.2)
Hydrophobic silica (trade name "R974" manufactured by NIPPON AEROSIL CO., LTD., specific gravity: 2.2)

<Silicone Oil>
Polyether-modified silicone oil 1 (trade name "FZ-2110" manufactured by Dow Corning Toray Co., Ltd., HLB value: 0, polyether-modified polyalkylsiloxane)
Polyether-modified silicone oil 2 (trade name "Y7006" manufactured by Dow Corning Toray Co., Ltd., HLB value: 2, polyether-modified polyalkylsiloxane)
Polyether-modified silicone oil 3 (trade name "FZ-2222" manufactured by Dow Corning Toray Co., Ltd., HLB value: 4, polyether-modified polyalkylsiloxane)
Polyether-modified silicone oil 4 (trade name "L-7001" manufactured by Dow Corning Toray Co., Ltd., HLB value: 5, polyether-modified polyalkylsiloxane)
Polyether-modified silicone oil 5 (trade name "SF8410" manufactured by Dow Corning Toray Co., Ltd., HLB value: 6, polyether-modified polyalkylsiloxane)
Polyether-modified silicone oil 6 (trade name "SH8400" manufactured by Dow Corning Toray Co., Ltd., HLB value: 8, polyether-modified polyalkylsiloxane)
Polyether-modified silicone oil 7 (trade name "SH3746" manufactured by Dow Corning Toray Co., Ltd., HLB value: 16, polyether-modified polyalkylsiloxane)

<Polyol>
Polyol 1 (trade name "NEWPOL PE-71" manufactured by Sanyo Chemical Industries, Ltd., polyoxyethylene polyoxypropylene glycol)
Polyol 2 (trade name "PREMINOL S3011" manufactured by NOF Corporation, polyoxypropylene glyceryl ether)

<Inorganic Powder>
Titanium oxide powder (trade name "A-100" manufactured by Ishihara Sangyo Kaisha, Ltd., specific gravity: 4)
Zinc oxide powder (trade name "Zncox Super F-2" manufactured by HAKUSUI TECH CO., LTD., specific gravity: 5.6)

Example 1

Preparation of a (Meth)Acrylic Acid Ester-Based Polymer:

2-Ethylhexyl acrylate and butyl acrylate were radically polymerized using the solution polymerization method in the presence of an azo-based polymerization initiator to obtain a (meth)acrylic acid ester-based polymer having fluidity at room temperature. Table 1 shows the weight average molecular weight, the viscosity at 25° C., and the specific gravity at 25° C. of the obtained (meth)acrylic acid ester-based polymer. The weight average molecular weight, the viscosity at 25° C., and the specific gravity at 25° C. of the (meth)acrylic acid ester-based polymer were measured using the above-described methods.

Preparation of a Composition for Separating Blood Serum or Blood Plasma:

The obtained (meth)acrylic acid ester-based polymer, hydrophilic silica, and hydrophobic silica were mixed at the blending proportions shown in Table 1, a polyether-modified silicone oil was added to the resulting mixture, and the components were further mixed to prepare a composition for separating blood serum or blood plasma.

Examples 2 to 4 and Comparative Examples 1 to 3

Compositions for separating blood serum or blood plasma were prepared as in Example 1, except that the weight average molecular weight, the viscosity at 25° C., and the specific gravity at 25° C. of the (meth)acrylic acid ester-based polymer having fluidity at room temperature were changed as shown in Table 1.

Examples 5 to 25 and Comparative Examples 4 to 6

Compositions for separating blood serum or blood plasma were prepared as in Example 1, except that the weight average molecular weight, the viscosity at 25° C., and the specific gravity at 25° C. of the (meth)acrylic acid ester-based polymer having fluidity at room temperature were changed as shown in Tables 2 and 3, and the types and amounts of the components blended were changed as shown in Tables 2 and 3.

The compositions for separating blood serum or blood plasma obtained in Examples 1 to 25 had the capability of separating blood serum or blood plasma from blood.

(Evaluation)

For the compositions for separating blood serum or blood plasma obtained in Examples 1 to 4 and Comparative Examples 1 to 3, the following (1) bubbling rate was evaluated. For the compositions for separating blood serum or blood plasma obtained in Examples 5 to 18 and Comparative Examples 4 to 6, the following (2) specific gravity, (3) flow (L value), and (4) phase separation were evaluated. For the compositions for separating blood plasma obtained in Examples 19 to 25, the following (2) specific gravity and (5) recovery of blood cell component-containing blood plasma were evaluated.

<(1) Bubbling Rate>

A blood collection container was prepared by housing 1.0 g of the obtained composition for separating blood serum or blood plasma in a bottomed PET tube (blood collection container body) having a length of 100 mm and an inner diameter of 14 mm of the opening, reducing the pressure inside the blood collection container to 5 kPa, and hermetically sealing the blood collection container with a butyl rubber stopper. For each example, 80 such blood collection containers were prepared. Each of these blood collection containers was irradiated with an electron beam at a dose of 10 kGy. The composition for separating blood serum or blood plasma immediately after the electron beam irradiation was visually observed, and the bubbling rate was calculated in accordance with the following equation:

bubbling rate (%)=(the number of blood collection containers in which the composition for separating blood serum or blood plasma bubbled)/(the number of blood collection containers irradiated with an electron beam)×100

<(2) Specific Gravity>

The specific gravity was measured by dropping one drop of the obtained composition for separating blood serum or blood plasma sequentially into saline solutions at 25° C. having specific gravities adjusted in a stepwise manner in increments of 0.002, and measuring the specific gravity based on floating and sinking in the saline solutions.

<(3) Flow (L Value)>

A blood collection container was prepared by housing 1.0 g of the obtained composition for separating blood serum or blood plasma in the bottom of a transparent bottomed PET tube (blood collection container body) having an inner diameter of 14 mm and a length of 100 mm, and closing the blood collection container with a butyl rubber stopper. Subsequently, centrifugation was performed at 3000 rpm for 5 minutes using an angle rotor having an angle of 45°, and the liquid surface of the composition for separating blood serum or blood plasma was adjusted to have an angle of about 45° with respect to the longitudinal direction of the bottomed PET tube. Next, the blood collection container was fixed on a rack so that the mouth side of the bottomed PET tube faced downward, and the liquid surface of the composition for separating blood serum or blood plasma had an angle of about 90° with respect to the horizontal direction. The blood collection container was held in this state and allowed to stand in an oven warmed at 35° C. for 5 days. By comparing the position of the upper edge of the liquid surface of the composition for separating blood serum or blood plasma before being allowed to stand and the position of the upper edge of the liquid surface of the composition for separating blood serum or blood plasma after being allowed to stand, the distance that the composition for separating blood serum or blood plasma flowed downward along the inner wall of the blood collection container body, between before and after being allowed to stand, was measured with a vernier caliper.

<(4) Phase Separation>

A blood collection container was prepared by housing 1.0 g of the obtained composition for separating blood serum or blood plasma in the bottom of a transparent bottomed PET tube (blood collection container body) having an inner diameter of 14 mm and a length of 100 mm, and closing the blood collection container with a butyl rubber stopper. Subsequently, centrifugation was performed at 3000 rpm for 5 minutes using an angle rotor having an angle of 45°, and the liquid surface of the composition for separating blood serum or blood plasma was adjusted to have an angle of about 45° with respect to the longitudinal direction of the bottomed PET tube. Next, the blood collection container was fixed on a rack so that the mouth side of the bottomed PET tube faced downward, and the liquid surface of the composition for separating blood serum or blood plasma had an angle of about 900 with respect to the horizontal direction. The blood collection container was held in this state and allowed to stand in an oven warmed at 35° C. for 10 days. The distance that the component exuded from the composition for separating blood serum or blood plasma flowed downward along the inner wall of the blood collection container, between before and after being allowed to stand, was measured with a vernier caliper.

<(5) Recovery of Blood Cell Component-Containing Blood Plasma>

Preparation of a Blood Collection Container:

A bottomed PET tube (blood collection container body) having a length of 100 mm and an inner diameter of 14 mm of the opening was prepared. 1.0 g of the obtained composition for separating blood plasma was housed in the blood collection container body. Ethylenediaminetetraacetic acid (EDTA) was adhered to the inner wall of the blood collection container body, the pressure inside the blood collection container was reduced to 5 kPa, and the blood collection container was hermetically sealed with a butyl rubber stopper. In this manner, the blood collection container in which the composition for separating blood plasma was housed in the blood collection container body was prepared.

Blood from three individuals was prepared, and the following steps were performed in order:

Blood-Collecting Step:

4 mL of the blood was collected into the blood collection container body of the obtained blood collection container.

Centrifuging Step:

The blood collection container was centrifuged at 1500 G for 30 minutes. After centrifugation, blood cell components positioned on the partition wall formed by the composition for separating blood plasma were suspended in blood plasma positioned above the blood cell components, and the blood plasma containing the blood cell components was recovered.

The recovered blood was analyzed using an automated multi-parameter blood cell analyzer ("XE5000" manufactured by Sysmex Corporation) to measure the number of cells of each of the blood cell components (red blood cells, neutrophils, eosinophils, basophils, lymphocytes, and monocytes) in the separated blood plasma. With respect to the prepared blood (whole blood samples) as well, the number of cells of each of the blood cell components (red blood cells, neutrophils, eosinophils, basophils, lymphocytes, and monocytes) in the whole blood samples was similarly measured. The concentration of each of the blood cell components is the average of the results obtained by evaluating the prepared blood from the three individuals.

For the compositions for separating blood plasma obtained in Examples 19 to 22, the red blood cell removal rate, the white blood cell recovery rate, the granulocyte removal rate, and the mononuclear cell recovery rate were each calculated in accordance with the following equation, and the recovery of white blood cells was evaluated based on the following determination criteria. For the compositions for separating blood plasma obtained in Examples 23 to 25, the recovery of white blood cells was evaluated based on the following determination criteria.

Red blood cell removal rate (%)=100−[(the number of red blood cells contained in the separated blood plasma)/(the number of red blood cells contained in the whole blood sample)×100)]

White blood cell recovery rate (%)=(the number of white blood cells contained in the separated blood plasma)/(the number of white blood cells contained in the whole blood sample)×100

Granulocyte removal rate (%)=100−[(the number of granulocytes contained in the separated blood plasma)/(the number of granulocytes contained in the whole blood sample)×100)]

Mononuclear cell recovery rate (%)=(the number of mononuclear cells contained in the separated blood plasma)/(the number of mononuclear cells contained in the whole blood sample)×100

[Determination Criteria for Recovery of White Blood Cells]

○: The proportion of the number of red blood cells contained in the separated blood plasma with respect to the number of red blood cells contained in the whole blood before separation is 10% or less, and the proportion of the number of white blood cells contained in the separated blood plasma with respect to the number of white blood cells contained in the whole blood before separation is 25% or more.

X: The proportion of the number of red blood cells contained in the separated blood plasma with respect to the number of red blood cells contained in the whole blood before separation is above 10%, or the proportion of the number of white blood cells contained in the separated blood plasma with respect to the number of white blood cells contained in the whole blood before separation is less than 25%.

The compositions and the results are shown in Tables 1 to 3 below.

TABLE 1

| | (Meth)acrylic acid ester-based polymer having fluidity at room temperature | | | | Silica fine powder | | | | | Silicone oil | | | | Evaluation |
|---|---|---|---|---|---|---|---|---|---|---|---|---|---|---|
| | Weight average molecular weight | % by weight | Viscosity (25° C.) Pa·s | Specific gravity (25° C.) | Hydrophilic silica Trade name | % by weight | Hydrophobic silica Trade name | % by weight | Total content % by weight | Trade name | HLB value | % by weight | Total % by weight | Bubbling rate % |
| Example 1 | 27000 | 97.45 | 65 | 1.031 | 200CF | 1.7 | R974 | 0.4 | 2.1 | SF8410 | 6 | 0.45 | 100 | 0 |
| Example 2 | 22000 | 97.45 | 73 | 1.032 | 200CF | 1.7 | R974 | 0.4 | 2.1 | SF8410 | 6 | 0.45 | 100 | 0 |
| Example 3 | 18000 | 97.45 | 98 | 1.033 | 200CF | 1.7 | R974 | 0.4 | 2.1 | SF8410 | 6 | 0.45 | 100 | 5 |
| Example 4 | 15000 | 97.45 | 102 | 1.031 | 200CF | 1.7 | R974 | 0.4 | 2.1 | SF8410 | 6 | 0.45 | 100 | 8 |
| Comparative Example 1 | 9000 | 97.45 | 70 | 1.031 | 200CF | 1.7 | R974 | 0.4 | 2.1 | SF8410 | 6 | 0.45 | 100 | 11 |
| Comparative Example 2 | 5000 | 97.45 | 87 | 1.030 | 200CF | 1.7 | R974 | 0.4 | 2.1 | SF8410 | 6 | 0.45 | 100 | 11 |
| Comparative Example 3 | 4000 | 97.45 | 50 | 1.032 | 200CF | 1.7 | R974 | 0.4 | 2.1 | SF8410 | 6 | 0.45 | 100 | 15 |

TABLE 2

| | (Meth)acrylic acid ester-based polymer having fluidity at room temperature | | | | Silica fine powder | | | | | Silicone oil |
|---|---|---|---|---|---|---|---|---|---|---|
| | Weight average molecular weight | % by weight | Viscosity (25° C.) Pa·s | Specific gravity (25° C.) | Hydrophilic silica Trade name | % by weight | Hydrophobic silica Trade name | % by weight | Total content % by weight | Trade name |
| Example 5 | 20000 | 97.45 | 78 | 1.034 | 200CF | 1.7 | R974 | 0.4 | 2.1 | FZ-2110 |
| Example 6 | 20000 | 97.45 | 78 | 1.034 | 200CF | 1.7 | R974 | 0.4 | 2.1 | Y7006 |
| Example 7 | 20000 | 97.45 | 78 | 1.034 | 200CF | 1.7 | R974 | 0.4 | 2.1 | FZ-2222 |
| Example 8 | 20000 | 97.45 | 78 | 1.034 | 200CF | 1.7 | R974 | 0.4 | 2.1 | L-7001 |
| Example 9 | 20000 | 97.45 | 78 | 1.034 | 200CF | 1.7 | R974 | 0.4 | 2.1 | SF8410 |
| Example 10 | 20000 | 97.35 | 78 | 1.034 | 200CF | 2 | R974 | 0.2 | 2.2 | SF8410 |
| Example 11 | 20000 | 97.85 | 78 | 1.034 | 200CF | 1.7 | — | — | 1.7 | SF8410 |
| Example 12 | 20000 | 97.35 | 78 | 1.034 | 200CF | 1.6 | R974 | 0.6 | 2.2 | SF8410 |
| Example 13 | 20000 | 97.75 | 78 | 1.034 | 200CF | 1.7 | R974 | 0.4 | 2.1 | SF8410 |
| Example 14 | 20000 | 97.6 | 78 | 1.034 | 200CF | 1.7 | R974 | 0.4 | 2 1 | SF8410 |
| Example 15 | 20000 | 97.3 | 78 | 1.034 | 200CF | 1.7 | R974 | 0.4 | 2.1 | SF8410 |
| Example 16 | 20000 | 96.1 | 78 | 1.034 | 200CF | 1.7 | R974 | 0.4 | 2.1 | SF8410 |
| Example 17 | 20000 | 97.45 | 78 | 1.034 | 200CF | 1.7 | R974 | 0.4 | 2.1 | SH8400 |
| Example 18 | 20000 | 97.45 | 78 | 1.034 | 200CF | 1.7 | R974 | 0.4 | 2.1 | SH3746 |
| Comparative Example 4 | 20000 | 99.55 | 78 | 1.034 | — | — | — | — | — | SF8410 |
| Comparative Example 5 | 20000 | 97.9 | 78 | 1.034 | 200CF | 1.7 | R974 | 0.4 | 2.1 | — |
| Comparative Example 6 | 20000 | 97.15 | 78 | 1.034 | 200CF | 1.7 | R974 | 0.4 | 2.1 | — |

TABLE 2-continued

|  | Silicone oil | | Polyol | | | | Total | | Evaluation | |
|---|---|---|---|---|---|---|---|---|---|---|
|  | HLB value | % by weight | Trade name | % by weight | Trade name | % by weight | % by weight | Specific gravity | Flow (L value) mm | Phase separation mm |
| Example 5 | 0 | 0.45 | — | — | — | — | 100 | 1.044 | 46 | 30 |
| Example 6 | 2 | 0.45 | — | — | — | — | 100 | 1.044 | 0.2 | 5.7 |
| Example 7 | 4 | 0.45 | — | — | — | — | 100 | 1.044 | 0.5 | 4.2 |
| Example 8 | 5 | 0.45 | — | — | — | — | 100 | 1.044 | 0.5 | 6.7 |
| Example 9 | 6 | 0.45 | — | — | — | — | 100 | 1.044 | 0.3 | 1.1 |
| Example 10 | 6 | 0.45 | — | — | — | — | 100 | 1.044 | 0.2 | 1.2 |
| Example 11 | 6 | 0.45 | — | — | — | — | 100 | 1.041 | 0.2 | 0.7 |
| Example 12 | 6 | 0.45 | — | — | — | — | 100 | 1.044 | 0.4 | 0.8 |
| Example 13 | 6 | 0.15 | — | — | — | — | 100 | 1.044 | 0.2 | 15 |
| Example 14 | 6 | 0.3 | — | — | — | — | 100 | 1.044 | 0.1 | 0.4 |
| Example 15 | 6 | 0.6 | — | — | — | — | 100 | 1.044 | 0.1 | 0.2 |
| Example 16 | 6 | 1.8 | — | — | — | — | 100 | 1.044 | 0.1 | 0.2 |
| Example 17 | 8 | 0.45 | — | — | — | — | 100 | 1.044 | 0.4 | 9.9 |
| Example 18 | 16 | 0.45 | — | — | — | — | 100 | 1.044 | 0.3 | 23 |
| Comparative Example 4 | 6 | 0.45 | — | — | — | — | 100 | 1.034 | >80 | * |
| Comparative Example 5 | — | — | — | — | — | — | 100 | 1.044 | >80 | * |
| Comparative Example 6 | — | — | NEW-POLPE-71 | 0.25 | PRE-MINOLS3001 | 0.50 | 100 | 1.044 | 23 | 54 |

* Because the composition for separating blood serum or blood plasma flowed to the mouth of the bottomed PET tube, the distance that the component exuded from the composition for separating blood serum or blood plasma flowed could not be measured.

TABLE 3

|  |  |  |  |  | Example 19 | Example 20 | Example 21 | Example 22 |
|---|---|---|---|---|---|---|---|---|
| (Meth)acrylic acid ester-based polymer having fluidity at room temperature | | | Specific gravity: 1.034 | % by weight | 94.65 | 93.45 | 92.30 | 91.65 |
| | | | Specific gravity: 1.050 | % by weight | 0 | 0 | 0 | 0 |
| Silica fine powder | | Hydrophilic silica | 200CF | % by weight | 0.75 | 0.75 | 0.6 | 0.5 |
| | | Hydrophobic silica | R974 | % by weight | 2.45 | 2.45 | 2.55 | 2.7 |
| Silicone oil | | | SF8410 | % by weight | 0.15 | 0.15 | 0.15 | 0.15 |
| Titanium oxide powder | | | A-100 | % by weight | 2 | 3.2 | 4.4 | 5 |
| Zinc oxide powder | | | Zncox Super F-2 | % by weight | 0 | 0 | 0 | 0 |
| | | Total | | % by weight | 100 | 100 | 100 | 100 |
| Evaluation | | Specific gravity | | | 1.068 | 1.078 | 1.088 | 1.093 |
| | Recovery of blood cell component-containing blood plasma | The numbers of blood cell components in the separated blood plasma or in the whole blood sample | Red blood cells | cells | 53333333 | 66666667 | 266666667 | 800000000 |
| | | White blood cells | Granulocytes Neutrophils | cells | 704000 | 1905778 | 10181333 | 11444000 |
| | | | Eosinophils | cells | 0 | 29778 | 306667 | 458000 |
| | | | Basophils | cells | 21333 | 29778 | 0 | 0 |
| | | Mononuclear cells | Lymphocytes | cells | 4949333 | 6044889 | 6685333 | 6338000 |
| | | | Monocytes | cells | 725333 | 923111 | 1226667 | 960000 |
| | | Total | | cells | 6399999 | 8933334 | 18400000 | 19200000 |
| | Red blood cell removal rate | | | % | 100 | 100 | 98 | 95 |
| | White blood cell recovery rate | | | % | 32 | 45 | 92 | 96 |
| | Granulocyte removal rate | | | % | 94 | 84 | 15 | 4 |
| | Mononuclear cell recovery rate | | | % | 75 | 92 | 104 | 96 |
| | White blood cell collection | | | Determination | ○ | ○ | ○ | ○ |

|  |  |  |  |  | Example 23 | Example 24 | Example 25 | Whole blood sample |
|---|---|---|---|---|---|---|---|---|
| (Meth)acrylic acid ester-based polymer having fluidity at room temperature | | | Specific gravity: 1.034 | % by weight | 94.85 | 93.75 | 0 | — |
| | | | Specific gravity: 1.050 | % by weight | 0 | 0 | 95.45 | — |

TABLE 3-continued

| | | | | | | | | | |
|---|---|---|---|---|---|---|---|---|---|
| | Silica fine powder | | Hydrophilic silica | 200CF | % by weight | 0.75 | 0.75 | 0.75 | — |
| | | | Hydrophobic silica | R974 | % by weight | 2.45 | 2.45 | 2.45 | — |
| | Silicone oil | | | SF8410 | % by weight | 0.15 | 0.15 | 0.15 | — |
| | Titanium oxide powder | | | A-100 | % by weight | 0 | 0 | 1.2 | — |
| | Zinc oxide powder | | | Zncox Super F-2 | % by weight | 1.8 | 2.9 | 0 | — |
| | Total | | | | % by weight | 100 | 100 | 100 | — |
| Evaluation | Specific gravity | | | | | 1.068 | 1.078 | 1.078 | — |
| Recovery of blood cell component-containing blood plasma | The numbers of blood cell components in the separated blood plasma or in the whole blood sample | White blood cells | Red blood cells | | | — | — | — | 17426666667 |
| | | | Granulocytes | Neutrophils | | — | — | — | 11733333 |
| | | | | Eosinophils | | — | — | — | 466667 |
| | | | | Basophils | | — | — | — | 200000 |
| | | | Mononuclear cells | Lymphocytes | | — | — | — | 6466667 |
| | | | | Monocytes | | — | — | — | 1133333 |
| | | | | Total | | — | — | — | 20000000 |
| | Red blood cell removal rate | | | | % | — | — | — | — |
| | White blood cell recovery rate | | | | % | — | — | — | — |
| | Granulocyte removal rate | | | | % | — | — | — | — |
| | Mononuclear cell recovery rate | | | | % | — | — | — | — |
| | White blood cell collection | | | | Determination | ○ | ○ | ○ | — |

As is clear from Table 1, when the weight average molecular weight of the (meth)acrylic acid ester-based polymer was 15000 or more, bubbling during sterilization was effectively inhibited.

As is clear from Table 2, when all of the (meth)acrylic acid ester-based polymer, the silica fine powder, and the silicone oil were contained, phase separation of the composition for separating blood serum or blood plasma was effectively inhibited. In particular, when the HLB of the silicone oil was 1 or more and 10 or less, phase separation of the composition for separating blood serum or blood plasma was more effectively inhibited. Furthermore, when the content of the silicone oil was 0.10% by weight or more and 2.00% by weight or less, phase separation of the composition for separating blood serum or blood plasma was even more effectively inhibited.

As is clear from Table 3, by adjusting the specific gravity of the composition for separating blood plasma, red blood cells could be removed, and white blood cells could be recovered. Furthermore, in Examples 19 and 20, red blood cells and granulocytes could be removed, and mononuclear cells could be recovered.

In the compositions for separating blood serum or blood plasma obtained in Examples 1 to 4, the occurrence of phase separation was reduced. In the compositions for separating blood serum or blood plasma obtained in Examples 5 to 18, in which the weight average molecular weight of the (meth) acrylic acid ester-based polymer was 15000 or more, bubbling during sterilization was reduced. In the compositions for separating blood plasma obtained in Examples 19 to 25, bubbling during sterilization and the occurrence of phase separation were reduced.

The invention claimed is:

1. A composition for separating blood plasma comprising: a (meth)acrylic acid ester-based polymer, a silica fine powder, and a silicone oil, wherein
the (meth)acrylic acid ester-based polymer has fluidity at room temperature, and has a weight average molecular weight of 15000 or more and 100000 or less,
a content of the silicone oil is 0.10% by weight or more and 2.00% by weight or less,
the composition for separating blood plasma separates white blood cell-containing blood plasma from blood, and
the composition for separating blood plasma has a specific gravity at 25° C. of greater than 1.060 and 1.095 or less.

2. The composition for separating blood plasma according to claim 1, wherein the silicone oil is a polyether-modified polyalkylsiloxane.

3. The composition for separating blood plasma according to claim 1, wherein the silicone oil has an HLB value of 1 or more and 10 or less.

4. The composition for separating blood plasma according to claim 1, wherein the silica fine powder comprises hydrophilic silica.

5. The composition for separating blood plasma according to claim 4, wherein a content of the hydrophilic silica is 0.3% by weight or more and 2.20% by weight or less.

6. The composition for separating blood plasma according to claim 4, wherein the silica fine powder comprises hydrophilic silica and hydrophobic silica.

7. The composition for separating blood plasma according to claim 6, wherein a total content of the hydrophilic silica and the hydrophobic silica is 1.40% by weight or more and 4.0% by weight or less.

8. The composition for separating blood plasma according to claim 1, wherein the composition comprises an inorganic powder different from the silica fine powder.

9. The composition for separating blood plasma according to claim 1, wherein the composition has a specific gravity at 25° C. of 1.068 or more and 1.095 or less.

10. A blood collection container comprising:
a blood collection container body; and
the composition for separating blood plasma according to claim 1, wherein
the composition for separating blood plasma is housed in the blood collection container body.

11. A method for separating blood plasma using the blood collection container according to claim 10, comprising the steps of:
collecting blood into the blood collection container body; and centrifuging the blood collection container in which the blood has been collected.

12. The composition for separating blood plasma according to claim 1, wherein the (meth)acrylic acid ester-based polymer comprises at least one selected from the group consisting of (meth)acrylic acid alkoxyalkyl esters, (meth)acrylic acid hydroxyalkyl esters, (meth)acrylic acid glycidyl esters, (meth)acrylic acid dialkylaminoalkyl esters, (meth)acrylic acid benzyl esters, (meth)acrylic acid phenoxyalkyl esters, (meth)acrylic acid cyclohexyl esters, (meth)acrylic acid isobornyl esters, and (meth)acrylic acid alkoxysilylalkyl esters.

13. The composition for separating blood plasma according to claim 1, further comprising two or more colorants.

14. A composition for separating blood plasma comprising:
a (meth)acrylic acid ester-based polymer, a silica fine powder, and a silicone oil, wherein
the (meth)acrylic acid ester-based polymer has fluidity at room temperature, and has a weight average molecular weight of 15000 or more and 100000 or less,
a content of the silicone oil is 0.10% by weight or more and 2.00% by weight or less,
the composition for separating blood plasma separates mononuclear cell-containing blood plasma from blood, and
the composition has a specific gravity at 25° C. of greater than 1.060 and 1.085 or less.

15. A blood collection container comprising:
a blood collection container body; and
the composition for separating blood plasma according to claim 14, wherein
the composition for separating blood plasma is housed in the blood collection container body.

16. A method for separating blood plasma using the blood collection container according to claim 15, comprising the steps of:
collecting blood into the blood collection container body; and
centrifuging the blood collection container in which the blood has been collected.

* * * * *